United States Patent
Rardon et al.

(10) Patent No.: US 6,251,999 B1
(45) Date of Patent: Jun. 26, 2001

(54) TIN CARBOXYLATE CATALYSTS FOR EPOXY-ACID COATING COMPOSITIONS

(75) Inventors: Daniel E. Rardon, Gibsonia; Kurt A. Humbert, Allison Park; Karen A. Barkac, Murrysville; Peter Kamarchik, Jr., Saxonburg, all of PA (US); Mark E. Wozniak, Macon, GA (US)

(73) Assignee: PPG Industries Ohio, Inc., Cleveland, OH (US)

( * ) Notice: Subject to any disclaimer, the term of this patent is extended or adjusted under 35 U.S.C. 154(b) by 0 days.

(21) Appl. No.: 09/339,394

(22) Filed: Jun. 23, 1999

Related U.S. Application Data

(62) Division of application No. 08/997,282, filed on Dec. 23, 1997, now abandoned.

(51) Int. Cl.[7] .................................................... C08F 8/00
(52) U.S. Cl. ........................ 525/195; 502/170; 525/176; 525/438; 525/533
(58) Field of Search .................... 502/154, 161, 502/170, 227; 525/506, 533, 176, 438, 195

(56) References Cited

U.S. PATENT DOCUMENTS

| | | | |
|---|---|---|---|
| Re. 32,261 | 10/1986 | Hirota et al. ........................ 525/285 |
| 2,684,973 | 7/1954 | Mack et al. ......................... 260/429 |
| 2,933,459 | 4/1960 | Gurgiolo ................................. 260/2 |
| 3,208,955 | 9/1965 | Proops ................................... 260/2 |
| 3,773,694 | 11/1973 | Nakata et al. ...................... 260/2 A |
| 3,855,360 | 12/1974 | Shim ................................. 260/929 |
| 3,980,579 | 9/1976 | Syrop et al. ........................ 252/182 |
| 3,989,652 | 11/1976 | Shim ............................ 260/2.5 AR |
| 4,042,645 | 8/1977 | Hirota et al. ........................ 260/830 |
| 4,058,544 | 11/1977 | Kushlefsky ...................... 260/429.7 |
| 4,092,377 | 5/1978 | Shim ................................. 260/969 |
| 4,102,942 | 7/1978 | Smith et al. ........................ 260/836 |
| 4,119,593 | 10/1978 | Smith et al. ..................... 260/18 EP |
| 4,147,679 | 4/1979 | Scriven et al. ............... 260/29.2 TN |
| 4,174,339 | 11/1979 | Matsuda et al. .................. 260/40 R |
| 4,220,679 | 9/1980 | Backhouse ......................... 427/401 |
| 4,270,953 | * 6/1981 | Nakagawa et al. ................. 524/440 |
| 4,281,076 | 7/1981 | Kamimura ........................... 525/934 |
| 4,395,528 | 7/1983 | Leiner et al. ......................... 528/45 |
| 4,403,003 | 9/1983 | Backhouse ........................ 427/407.1 |
| 4,407,997 | 10/1983 | Sghibartz ............................ 524/202 |
| 4,426,464 | 1/1984 | Sgibartz ............................. 523/122 |
| 4,451,573 | 5/1984 | Ikegami et al. ..................... 502/113 |
| 4,554,185 | 11/1985 | Lane et al. ....................... 427/385.5 |
| 4,596,724 | 6/1986 | Lane et al. ....................... 427/385.5 |
| 4,650,718 | 3/1987 | Simpson et al. .................... 428/413 |
| 4,681,811 | 7/1987 | Simpson et al. .................... 428/413 |
| 4,764,430 | 8/1988 | Blackburn et al. ................. 428/413 |
| 4,927,868 | 5/1990 | Schimmel et al. ................. 523/439 |
| 4,981,924 | 1/1991 | Nichols et al. ..................... 525/528 |
| 4,987,244 | 1/1991 | Nichols et al. ....................... 556/29 |
| 5,071,904 | 12/1991 | Martin et al. ....................... 524/458 |
| 5,196,485 | 3/1993 | McMonigal et al. ............. 525/327.3 |
| 5,384,367 | 1/1995 | Swarup et al. ...................... 525/169 |
| 5,407,707 | 4/1995 | Simeone et al. .................... 427/410 |
| 5,969,058 | * 10/1999 | Anderson et al. ................ 525/111.5 |

FOREIGN PATENT DOCUMENTS

| | | |
|---|---|---|
| 0643112 | 3/1995 | (EP) . |
| 2131416 | 3/1995 | (CA) . |
| 6606272 | 5/1966 | (NL) . |
| WO99/32496 | 7/1999 | (WO) . |

OTHER PUBLICATIONS

*Synthesis of Triaryltin Hydrides* by Stern & Becker, Nov. 1964, pp. 3221–3225.

Principles of Polymer Chemistry (1953) Cornell University Press, pp. 52–57.

* cited by examiner

*Primary Examiner*—Robert E. L. Sellers
(74) *Attorney, Agent, or Firm*—Deborah M. Altman; Jacques B. Miles

(57) ABSTRACT

A catalytic tin carboxylate adduct, which is useful as a catalyst in epoxy-acid coating compositions, is the reaction product of (A) a mono-, di-, or poly-carboxylic acid functional compound and (B) an organotin compound containing one to three aryl groups and at least one halogen or hydroxyl group attached to the tin atom. There is also provided an epoxy-acid coating composition, which incorporates this catalytic tin carboxylate adduct. The epoxy-acid coating composition is advantageous as an automotive topcoat, particularly as a clear coat composition because it exhibits good appearance, durability, stability and generates no, or extremely low levels of benzene during the curing process.

13 Claims, No Drawings

TIN CARBOXYLATE CATALYSTS FOR EPOXY-ACID COATING COMPOSITIONS

CROSS REFERENCE TO RELATED PATENT APPLICATION

This patent application is a division of U.S. patent application Ser. No. 08/997,282, filed Dec. 23, 1997, abandoned.

CROSS REFERENCE TO OTHER PATENT APPLICATIONS

This patent application is filed on the same day as the patent application entitled "Color-Plus-Clear Composite Coating Composition Containing Tin Catalysts" (Anderson, et. al.)

The present invention relates to catalyst compositions. More specifically, to catalyst compositions that are useful in epoxy-based film-forming coating compositions containing polyacid curing agents.

Epoxy-acid coating compositions may be powder coating compositions or liquid coating compositions and are well known in the art. Typical examples of epoxy-acid coating compositions are described in U.S. Pat. Nos. 4,650,718; 5,196,485 and 5,407,707: Epoxy-acid coating compositions are useful as clear topcoats or colored basecoats in color-plus-clear coating systems and have become increasingly popular as original finishes on motor vehicles such as automobiles, trucks and motorcycles. Epoxy-acid coating compositions may be cured at elevated temperatures after being applied to a ware such as an automobile. Catalysts may be present in the epoxy-acid coating compositions to accelerate the cure of the coating. Typically, tertiary amines are used as catalysts; however, some organotin compounds may also be used as catalysts in these epoxy-acid coating compositions.

One particularly useful organotin catalyst is triphenyltin hydroxide, hereinafter referred to as "TPTOH". A major problem associated with the use of TPTOH is the evolution of benzene during the curing process. Benzene is known to be environmentally undesirable and, as such, there are stringent regulations on the allowed amount of benzene released into the atmosphere from any given source. Because of the high volumes of air exiting typical automobile paint curing ovens and the relatively low levels of benzene evolved during the paint curing process, it is considered technologically and economically unfeasible to treat the exiting oven air for the removal of benzene.

The use of some organotin compounds as catalysts are known in the art. For example, U.S. Pat. No. 3,773,694 to Nakata, et al. discloses a polymerization catalyst for use in the polymerization of vicinal alkylene oxides, which is a reaction product of an organotin compound and an ester of an oxyacid of phosphorous or an acetyl derivative of (HO)$_3$PO. It is known that automotive coating compositions containing phosphites may have poor exterior durability. Additionally, it is known in the art that compounds with P-O-C linkages, such as those disclosed in Nakata, are prone to hydrolysis which may lower the humidity resistance of coatings containing these compounds.

SUMMARY OF THE INVENTION

It is an object of the present invention to provide an organotin catalyst that is suitable for use in epoxy-acid coating compositions and that is effective at reduced concentrations, such that the coating compositions have good appearance, stability and durability, and evolve no, or extremely low levels of benzene during the curing process of the applied coating. By "extremely low levels of benzene", it is meant less than 20 parts per million (hereinafter referred to as "ppm").

It is another object of the invention to provide epoxy-acid coating compositions which have good appearance, durability and stability, and that evolve no, or extremely low levels of benzene during the curing process of the applied epoxy-acid coating composition.

These and other objects of the invention are achieved by the development of a tin carboxylate adduct which is useful as a catalyst in epoxy-acid coating compositions and which will generate no, or extremely low levels of benzene during the curing process of the coating in which it is used. The tin carboxylate adduct is comprised of the reaction product of (A) a compound with mono-, di-, or poly-carboxylic acid functionality and (B) an organotin compound containing one to three aryl groups and at least one halogen or hydroxyl group attached to the tin atom.

There is also provided an epoxy-acid coating composition, which incorporates the catalytic tin carboxylate adduct described above, having good appearance, durability and stability and which generates no, or extremely low levels of benzene during the curing process of the applied coating composition.

DETAILED DESCRIPTION OF THE INVENTION

The catalytic tin carboxylate adduct of the present invention is formed by the reaction of (A) a carboxylic acid functional compound having at least one carboxyl group and (B) an organotin compound having the general formula:

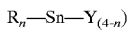

$$R_n-Sn-Y_{(4-n)}$$

where R is an aryl group, Y is a halogen or hydroxyl group, and n is an integer from 1 to 3. Suitable aryl groups include tolyl, napthyl, phenyl, and substituted phenyl such as 4-ethylphenyl, 3,5-dimethylphenyl, and 4-methoxyphenyl. Preferably, R is a phenyl group and Y is a hydroxyl group.

Preferably, the carboxylic acid functional compound used has the general formula:

$$R'(COOH)_m$$

where R' is a mono, di or polyvalent alkyl or aryl radical and m is an integer from 1 to 4.

In the practice of this invention, the carboxylic acid functional compound may be a mono-, di-, or poly-carboxylic acid; however, dicarboxylic acids are preferred. Some nonlimiting examples of suitable carboxylic acids include isostearic acid, lauric acid, tridecanoic acid, myristic acid, palmitic acid, adipic acid, succinic acid, pimelic acid, suberic acid, azelaic acid, sebacic acid, dodecanedioic acid, terephthalic acid, isophthalic acid, phthalic acid, tetrahydrophthalic acid and hexahydrophthalic acid. A preferred dicarboxylic acid used in the practice of this invention is dodecanedioic acid. Additionally, the carboxylic acid functional compound may be an acid functional polymer such as an acrylic, polyester or polyurethane polymer containing at least one carboxylic group per molecule. Carboxylic acid functional polyesters and half-acid esters can be used which are based on the condensation of aliphatic polyols with aliphatic and/or aromatic polycarboxylic acids or anhydrides, or the reaction of aliphatic polyols and aliphatic and/or aromatic anhydrides, respectively. Examples of suitable aliphatic polyols include ethylene glycol, propylene glycol, butylene glycol, 1,6-hexanediol, trimethylol propane, di-trimethylol propane, neopentyl glycol, 1,4-cyclohexanedimethanol, pentaerythritol and the like. The polycarboxylic acids and anhydrides may include, terephthalic acid, isophthalic acid, phthalic acid, phthalic anhydride, tetrahydrophthalic acid, tetrahydrophthalic anhydride, hexahydrophthalic acid, alkylhexahydrophthalic anhydride, chlorendic anhydride and the like.

The organotin compound used in the practice of this invention may contain one to three aryl groups attached to the tin atom. Preferably, the organotin compound contains three aryl groups. Suitable, but nonlimiting examples of organotin compounds include triphenyltin hydroxide, tritolyltin hydroxide, triphenylchlorotin, triphenylbromotin, tritolylchlorotin, tritolylbromotin, tris-4-ethylphenyltin hydroxide, tris-3,5-dimethylphenyltin hydroxide, tris-4-methoxyphenyltin hydroxide and phenyltin trichloride. Preferably, the organotin compound is triphenyltin hydroxide.

The catalytic tin carboxylate adduct of the present invention is formed by reacting a carboxylic acid and an organotin compound, usually in an inert atmosphere. Typically, the mole ratio of carboxylic acid to organotin compound ranges from about 2:1 to 10:1, preferably from about 3:1 to 7:1. The reaction is normally carried out at elevated temperatures, preferably from about 120° C. to 160° C., more preferably from about 120° C. to 140° C. Preferably, the reaction is carried out in a nitrogen atmosphere at atmospheric pressure. When the organotin compound contains phenyl groups, a normal by-product of the reaction is benzene, which can be distilled off and removed from the reaction vessel. The reaction should be kept at elevated temperatures for a sufficient time to remove most of the benzene from the reaction product, typically from about 1 to 4 hours; however, longer or shorter times may be used.

It is believed, without any limitations of the invention, that the catalytic tin carboxylate formed by the reaction of a carboxylic acid compound and an organotin compound, is a mixture of a mono-aryltin tris-carboxylate and a di-aryltin di-carboxylate. The catalytic tin compound may be depicted by the following general formula:

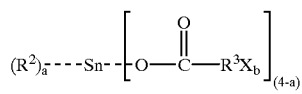

where $R^2$ is an aryl group, $R^3$ is a mono, di or polyvalent alkyl or aryl radical, X is a carboxyl group, a is 1 or 2, and b is an integer from 0 to 3.

In the mixture the ratio of tris-carboxylate to di-carboxylate may range from about 99:1 to 1:99. Preferably, there is more tris-carboxylate than di-carboxylate and typically the ratio may be from about 60:40 to 40:60, preferably from about 75:25 to 40:60, most preferably from 90:10 to 50:50.

The tin carboxylate adduct of the present invention may be a liquid or a solid, but preferably the adduct is a solid material. By being solid in nature, it can be easily incorporated into powder coating compositions. The adduct can also be incorporated into a liquid coating composition by dispersing the solid tin carboxylate adduct into the liquid coating like a pigment or flow control materials such as fumed silicas, micas, microgels and the like.

It is believed without any limitation of the invention that the solid tin carboxylate adduct becomes catalytically active after the adduct has melted, which normally occurs when the coating composition into which the adduct has been dispersed is cured, usually at elevated temperatures. This allows for both powder and liquid coating compositions having acceptable stability characteristics even at high levels of catalyst or with materials having higher catalytic activity. For example, in liquid epoxy-acid coating compositions the addition of higher levels of catalyst, or the use of a more catalytic material may improve appearance characteristics of the deposited film, such as gloss and distinctness of image (DOI). In typical epoxy-acid coating compositions, high levels of catalyst may be detrimental to the stability of the coating compositions. This is especially true for one package epoxy-acid coating compositions. In two package compositions the use of higher levels of catalyst normally is not a problem since the epoxy component and the acid curing agent are not mixed together until right before the coating is applied. The use of a solid catalyst that is unreactive with the liquid coating formulation until the catalyst melts during the cure of the deposited coating film allows for the addition of higher levels of catalyst, or the use of a more catalytic material in epoxy-acid coating compositions while maintaining acceptable stability characteristics.

Epoxy-acid powder coating compositions have used triphenyltin hydroxide (TPTOH) as a catalyst; however, as mentioned above the evolution of benzene during the curing process when TPTOH is used is undesirable. The use of a catalytic adduct of the present invention formed from the reaction of an organotin compound like TPTOH and a carboxylic acid functional compound, preferably dodecanedioic acid, solves this problem. The evolution of benzene is shifted from the curing process of the coating composition where the benzene cannot be economically removed from the exhaust air of typical paint curing ovens to the formation of the catalytic adduct. Benzene is a by-product of the reaction of organotin compounds containing phenyl groups such as TPTOH and a carboxylic acid functional compound. Since this reaction typically is carried out in an enclosed reaction vessel, the removal of the benzene can be accomplished easily and economically.

Tertiary amines and other organotin compounds have also proved to be useful as catalysts in epoxy-acid coatings compositions. Surprisingly, it has been found that the tin carboxylate adducts of the present invention are more catalytic in nature than most of the tertiary amines or organotin compounds the adducts may replace in epoxy-acid coating compositions. As a result, lower levels of the tin carboxylate adducts may be used in the coating compositions to achieve equivalent or superior cure properties. Typically, organotin compounds and tertiary amines are used in epoxy-acid coatings compositions at a level of about 0.5 to 5.0 weight percent based on total solids of the coating composition. The tin carboxylate adducts of the present invention are useful catalysts at a level of about 0.05 to 4.0 percent, preferably from about 0.1 to 2.0 weight percent based on total solids of the coating composition.

The epoxy-acid coating compositions mentioned above are generally the polyepoxide and polyacid type of curable coating compositions known in the art as solvent-borne, water-borne, or powder coating film-forming formulations. The water-borne coatings include those that are water-dilutable, where film-forming binders are either molecular dispersed solutions in water or water/solvent blends or binders in the form of dispersions or emulsions. By the term "film forming", it is meant that the resinous material upon drying or melting or curing at ambient or elevated temperature forms a self-supporting continuous film on the surface of a substrate, and includes polymeric materials that upon removal of any solvents or carriers present can coalesce to form a continuous film. Also, by the term "powder", it is meant a particulate, finely divided solid polymeric material generally having a particle size of 0.005 to 100 microns.

The polyepoxides which may be used include epoxy-containing acrylic polymers, epoxy condensation polymers such as polyglycidyl ethers of alcohols and phenols, certain polyepoxide monomers and oligomers, and mixtures of the foregoing. Epoxy condensation polymers such as polyglycidyl ethers of alcohols and phenols may be used such as those described in U.S. Pat. No. 4,650,718, column 5, lines 41 through 58. Suitable epxoy-containing acrylic polymers are copolymers of an ethylenically unsaturated monomer having at least one epoxy group and at least one polymerizable ethylenically unsaturated monomer which is free of epoxy groups.

Ethylenically unsaturated monomers containing epoxy groups suitable for use in the epoxy copolymer are those containing 1,2-epoxy groups as are known to those skilled in the art. Nonexclusive examples include glycidyl acrylate, glycidyl methacrylate, 3,4-epoxycyclohexylmethyl(meth)acrylate; 2-(3,4-epoxycyclohexyl)ethyl (meth)acrylate and allyl glycidyl ether. The epoxy group-containing ethylenically unsaturated monomer is preferably used in amounts of from about 30 to 70 and more preferably about 40 to 70 percent by weight of the total monomers used in preparing the epoxy-containing acrylic copolymer. Ethylenically unsaturated monomers which do not contain epoxy groups can be any such monomers known to those skilled in the art that can react by free radical addition polymerization with epoxy-containing unsaturated monomers to form a copolymer with epoxy functionality. Nonexclusive examples of such ethylenically unsaturated monomers which do not contain epoxy groups are alkyl esters of acrylic and methacrylic acid containing from 1 to 20 atoms in the alkyl group. Specific examples of these acrylates and methacrylates include: ethyl acrylate, butyl acrylate, 2-ethylhexyl acrylate, cyclohexyl acrylate, benzyl acrylate, isobornyl acrylate, methyl methacrylate, ethyl methacrylate, butyl methacrylate, isobornyl methacrylate, isodecyl methacrylate, cyclohexyl methacrylate, benzyl methacrylate, and mixtures 'thereof. Examples of other copolymerizable ethylenically unsaturated monomers are vinyl aromatic compounds such as styrene and vinyl toluene, nitriles such as acrylonitrile and methacrylonitrile; vinyl and vinylidene halides such as vinyl chloride and vinylidene fluoride and vinyl esters such as vinyl acetate, vinyl propionate, and vinyl pivalate; hydroxyl functional free radical polymerizable monomers like hydroxyethyl methacrylate, hydroxyethyl acrylate, hydroxypropyl methacrylate, hydroxypropyl acrylate, hydroxybutyl methacrylate, and hydroxybutyl acrylate; and alkoxysilane monomers having free radical polymerizable functionality such as the vinyl-containing alkoxy silane like trialkoxy vinylsilane, methacrylate-functional silanes like polyalkoxysilylalkyl methacrylate such as trimethoxysilylpropyl methacrylate and other silanes that are free radically polymerizable such as those having the general formula $R_x$—Si—$R'_{(4-x)}$) where R is an organo group such as alkyl and/or alkoxy groups along with the aforedescribed type of unsaturation and R' is an alkyl and/or alkoxy group generally with 1 to 10 carbon atoms, and x is an integer of 1 or 2.

The epoxy copolymer can be prepared generally by any method known to those skilled in the art but preferably by solution polymerization techniques in the presence of suitable catalysts such as organic peroxides, such as di-t-amyl peroxide, t-butyl perbenzoate, t-amyl peracetate, t-butyl peracetate or ethyl-3,3-di(t-amylperoxy) butyrate or azo compounds, such as benzoyl peroxide, N,N'-azobis (isobutyronitrile) or alpha, alpha-dimethylazobis (isobutyronitrile). Other free radical polymerization methods and other catalysts or initiators known to those skilled in the art for preparing epoxy copolymers can also be used. The polymerization can be carried out in an organic solution in which the monomers are soluble as known to those skilled in the art. Suitable solvents are aromatic solvents such as xylene toluene and mixtures thereof, ketones such as methyl amyl ketone or ester solvents such as ethyl 3-ethoxypropionate. Also other materials may be present for or during the polymerization; for example, a chain transfer agent such as alpha-methyl styrene dimer is preferably present in conventional chain transfer amounts. Generally, such a polymerization process is disclosed along with additional examples of both ethylenically unsaturated monomers with and without epoxy functionality in U.S. Pat. No. 4,681,811.

In addition to the epoxy copolymers described above, certain polyepoxide monomers and oligomers can also be present. Examples of these materials are described in U.S. Pat. No. 4,102,942 in column 3, lines 1–16. Specific examples of low molecular weight polyepoxides are 3,4-epoxycyclohexylmethyl 3,4-epoxycyclohexanecarboxylate and bis(3,4-epoxycyclohexyhnethyl) adipate.

These low molecular weight polyepoxides may be used to increase the cure response and solids content of the curable compositions. When used, they are present in amounts up to 30, preferably 5 to 30 percent by weight based on the total weight of resin solids in the curable composition. The epoxy copolymers typically have a range of molecular weights and a range of glass transition temperatures (Tg). For instance, the weight average molecular weight can be between about 1000 and 20,000, preferably about 1000 to 10,000, and more preferably about 1000 to 5000. The molecular weight is determined by gel permeation chromatography using a polystyrene standard. Preferably, the epoxy copolymers for liquid coatings have a glass transition temperature (Tg) less than 50° C., more preferably less than 30° C., but for powder coatings epoxy copolymers having higher Tg's can be used. The Tg is described in PRINCIPLES OF POLYMER CHEMISTRY, Flory, Cornell University Press, Ithaca, N.Y., 1953, pages 52–57. The Tg can be calculated as described by *Fox in Bull. Amer. Physic. Society* 1, 3, page 123 (1956). The actual measured values for Tg are obtainable by differential scanning calorimetry (DSC) usually at a rate of heating of 18° F. (10° C.) per minute, where the Tg is taken at the first inflection point. Also, the Tg can be measured experimentally by using a penetrometer such as a DuPont 940 Thermomedian Analyzer. The Tg of the polymers as used herein refers to the calculated values unless otherwise indicated.

The epoxy-acid coating compositions further include a polyacid component having a high average acid functionality. More specifically, the polyacid curing agent on average contains greater than two acid groups per molecule, more preferably three or more and most preferably, four or more, such acid groups being reactive with the polyepoxide to form a cured or crosslinked coating as indicated by its resistance to organic solvent. The parameter of greater than two acid groups per molecule is intended to encompass polyacid curing agents that are di-functional curing agents and tri- or higher functionality polyacid curing agents and mixtures thereof Polyacid curing agent mixtures including up to about 50 percent of a di-functional curing agent with a tri-functional curing agent are suitable. Also higher percentages of di-functional material can be useful alone or with the remainder of the curing agent mixtures as higher than tri-functional or when the polyepoxide component is highly functional. The acid functionality is preferably carboxylic acid, although acids such as phosphorus-based acid pay be used. When the epoxy-acid coating composition is a powder coating, the polyacid can be 1,12-dodecanedicarboxylic acid. For liquid coating compositions, preferably, the polyacid curing agent is a carboxylic acid terminated material having, on average, greater than two carboxylic acid groups per molecule. Among the polyacid curing agents which may be used include carboxylic acid group-containing polymers such as acrylic polymers, polyesters, and polyurethanes; oligomers such as ester group-containing oligomers and monomers.

For liquid coating compositions, the preferred polyacid curing agents are ester group-containing oligomers. Examples include half-esters formed from reacting polyols and 1,2-acid anhydrides or acid functional polyesters derived from polyols and polyacids or anhydrides. The half-esters are preferred because they are of relatively low molecular weight and are quite reactive with epoxy functionality enabling the formulation of high solids fluid compositions while maintaining outstanding properties such as gloss and distinctness of image. The half-esters are described in U.S. Pat. No. 5,384,367, column 8, line 41 to column 11, line 10, which is hereby incorporated by reference.

When the epoxy-acid coating composition is a powder coating, the polyacid is preferably a polycarboxylic acid. Preferably, the polycarboxylic acid is a crystalline material, more preferably a crystalline aliphatic material containing from 4 to 20 carbon atoms. Nonlimiting examples of suitable polycarboxylic acids include adipic, succinic, sebacic, azelaic and dodecanedioic acid. Preferably, the crystalline polycarboxylic acid is dodecanedioic acid.

Typically, the polyacid curing agent is present in the coating composition in amounts of about 10 to 90, preferably 20 to 50 percent by weight based on total weight of resin solids.

The epoxy-acid coating compositions may optionally contain an aminoplast resin. Aminoplast resins are condensation products of amines or amides with aldehydes. Examples of suitable amine or amides are melamine, benzoguanamine, urea and similar compounds. Generally, the aldehyde employed is formaldehyde, although products can be made from other aldehydes such as acetaldehyde and furfural. The condensation products contain methylol groups or similar alkylol groups depending on the particular aldehyde employed. Preferably, these methylol groups are etherified by reaction with an alcohol. Various alcohols employed include monohydric alcohols containing from I to 4 carbon atoms such as methanol, ethanol, isopropanol and n-butanol, with methanol being preferred. Aminoplast resins are commercially available from Cytec Industries, Inc. under the trademark CYMEL and from Monsanto Chemical Co. under the trademark RESIMENE. Typically, when used, the aminoplast resin is present in the composition in amounts up to about 30 percent by weight, more preferably from about 2 to 20 percent by weight based on total weight of resin solids in the coating composition. Also, blocked or unblocked isocyanate curing agents as are well known in the art can also be used in art recognized amounts. Also, mixtures of aminoplast resin and blocked isocyanate can be used.

Optionally, the coating composition can contain silane functionality which can be incorporated into the composition by using a reactive silane group-containing material, such as gamma-methacryloxypropyltrimethoxysilane or mercaptopropyltrimethoxysilane, which can be used in the preparation of the epoxy copolymers, as previously discussed. Such materials co-react with the polymerizing monomers or polymers forming a polymer with silane curing groups. Alternately, a silane group-containing material, such as methyltrimethoxysilane, in an amount up to 20, preferably 2 to 15 percent by weight based on resin solids, can be included in the composition.

The coating composition may optionally contain an aliphatic monocarboxylic acid containing at least 6, preferably from 8 to 22 carbon atoms such as described in U.S. Pat. No. 4,764,430, column 6, line 48, to column 7, line 9. Examples of such acids include lauric acid and isostearic acid. These monocarboxylic acids, when used, are present in amounts up to 15 percent, preferably 0.5 to 10 percent by weight based on total weight of resin solids of the coating composition.

The composition may also contain an anhydride, preferably an anhydride which is a liquid at 25° C. is used for liquid coating compositions. The presence of such an anhydride in the composition provides for improved cure response. Examples of suitable anhydrides include dodecenyl succinic anhydride and alkyl-substituted hexahydrophthalic anhydrides wherein the alkyl group contains up to 7 carbon atoms, more preferably up to 4 carbon atoms, such as methyl hexahydrophthalic anhydride. The amount of the anhydride which is used in the curable composition can vary from about 0 to 40 percent, preferably from about 5 to 25 percent by weight based on total weight of resin solids of the coating composition.

The epoxy-acid coating composition of the present invention may also contain a copolymer of an alpha olefin such as 1-octene or 1-decene and an olefinically unsaturated anhydride such as maleic anhydride. The anhydride group in such a polymer may be ring-opened with ethanol. The use of these copolymers in polyepoxide-polyacid curable compositions is described more fully in U.S. Pat. No. 4,927,868. When used, the copolymers are present in amounts up to percent, preferably 5 to 20 percent by weight based on total weight of resin solids of the coating composition.

Other optional ingredients, such as plasticizers, antioxidants, UV light absorbers and stabilizers may be formulated into the curable compositions of the present invention. When used, these ingredients are present (on an individual basis) in amounts up to 10 percent, preferably from about 0.1 to 5 percent by weight based on total weight of resin solids of the coating composition.

Besides the organotin adduct catalysts described above, the coating composition may have other catalysts to promote cure. A number of such catalysts are known in the art. These catalysts include basic materials such as secondary amine catalysts, for example, piperidine, and N-methyldodecylamine; tertiary amine catalysts such as N,N-dimethyldodecylamine, pyridine, methyldicocoamine and N,N-dimethylaniline; ammonium compounds, including tetrabutylammonium bromide, tetrabutylammonium hydroxide, and tetrabutylammonium acetate; phosphonium compounds, including ethyltriphenylphosphonium acetate and tetrabutyl phosphonium bromide, and other ammonium and phosphonium salts. When used, the catalysts are present in amounts up to 5, preferably 0.5 to 3 percent by weight based on total weight of resin solids of the coating composition.

The equivalent ratio of the reactants present in the epoxy-acid coating compositions are adjusted such that for each equivalent of carboxyl (anhydride, if present is considered monofunctional) there is 0.3 to 3.0, preferably 0.8 to 1.5 equivalent of epoxy.

The epoxy-acid coating compositions may be formulated into liquid high solids coating compositions; that is, compositions containing greater than 40 percent, preferably greater than 50 percent by weight resin solids. The solids content is determined by heating a sample of the composition to 110° C. for one hour to drive off the volatile material. Also, the coating compositions may be formulated as powder coating compositions. The powder coating compositions can be prepared by melt blending the ingredients. This can be accomplished by first blending the ingredients, including the catalytic tin carboxylate adduct of this invention, in a high shear mixer such as a planetary mixer, and then melt blending in an extruder from about 80° C. to about 130° C. The extrudate is then cooled and pulverized into a particulate blend.

The coating compositions may be applied to a substrate by any conventional coating technique such as brushing, spraying, dipping or flowing, but spray applications are preferred. Any of the known spraying techniques may be employed such as compressed air spraying, electrostatic spraying and either manual or automatic methods.

After application of the coating composition to the substrate, the coated substrate is heated to cure the coating. In the curing operation, solvents, when present, are driven off and the film-forming materials of the coating composition are crosslinked. The heating or curing operation is usually carried out at a temperature in the range of from 160° F. to 350° F. (71° C. to 177° C.) but if needed, lower or higher temperatures may be used as necessary to activate crosslinking mechanisms. The thickness of the coating is usually from about 0.5 to 5 mils (13 to 127 microns), preferably about 1.2 to 3 mils (30 to 76 microns).

Preferably, the compositions of the present invention are used to formulate clear coats for use in a color-plus-clear composite coatings. In a color-plus-clear composite coating, a pigmented or colored film-forming composition is applied to a substrate to form a base coat and a second film-forming composition is applied to the base coat to form a transparent top coat, or clear coat, over the base coat. The epoxy-acid coating compositions also can be used as the base coat of the composite coating composition where the coating would have the pigments and/or colorant added to it along with the typical additives of a base coat.

For a composite coating where the epoxy-acid coating composition is the clear coat, the film-forming composition of the base coat can be any of the compositions useful in coatings applications, particularly automotive applications. The film-forming composition of the basecoat comprises a resinous binder and a pigment to act as the colorant. Particularly useful resinous binders are acrylic polymers, polyesters, including alkyds, and polyurethanes.

The resinous binders for the base coat can be organic solvent-based materials such as those described in U.S. Pat. No. 4,220,679, note column 2, line 24 continuing through column 4, line 40. Also, water-based coating compositions such as those described in U.S. Pat. Nos. 4,403,003; 4,147,679 and 5,071,904 can be used as the binder in the base coat composition.

The base coat composition contains pigments to give it color. Suitable metallic pigments include aluminum flake, copper bronze flake and metal oxide coated mica.

Besides the metallic pigments, the base coat compositions may contain non-metallic color pigments conventionally used in surface coatings including inorganic pigments such as titanium dioxide, iron oxide, chromium oxide, lead chromate, and carbon black, and organic pigments such as phthalocyanine blue and phthalocyanine green.

Optional ingredients in the base coat composition are those which are well known in the art of formulating surface coatings and include surfactants, flow control agents, thixotropic agents, fillers, anti-gassing agents, organic co-solvents, catalysts, and other customary auxiliaries. Examples of these materials and suitable amounts are described in U.S. Pat. Nos. 4,220,679, 4,403,003; 4,147,769 and 5,071,904.

The base coating compositions can be applied over virtually any substrate including wood, metals, glass, cloth, plastic, foam, including elastomeric substrates and the like. They are particularly useful in applications over metals, particularly metals which are primed with an electrodeposition primer, and elastomeric substrates that are found on motor vehicles.

The base coat compositions can be applied to the substrate by any conventional coating technique such as brushing, spraying, dipping or flowing, but they are most often applied by spraying. The usual spray techniques and equipment for air spraying, airless spray and electrostatic spraying in either manual or automatic methods can be used.

During application of the base coat to the substrate, a film of the base coat is formed on the substrate typically in a thickness of about 0.1 to 5 mils (2.5 to 130 microns), preferably 0.1 to 2 mils (2.5 to 50 microns).

After forming a film of the base coat on the substrate, the base coat can be cured or alternately given a drying step in which solvent and/or water is driven out of the base coat film by heating or an air drying period before application of the clear coat. Suitable drying conditions will depend on the particular base coat composition, and on the ambient humidity if the composition is waterborne, but in general, a drying time of from about 1 to 15 minutes at a temperature of about 75° F. to 250° F. (21° C. to 121° C.) will be adequate. At the same time, the base coat film is adequately wetted by the topcoat composition so that satisfactory intercoat adhesion is obtained. Also, more than one base coat and multiple top coats may be applied to develop the optimum appearance. Usually between coats, the previously applied coat is flashed; that is, exposed to ambient conditions for about 1 to 20 minutes.

When the epoxy-acid coating composition is the clear coat in a composite coating, it is applied to the base coat by any of the conventional coating techniques mentioned above, with spray applications preferred. As mentioned above, the clear topcoat can be applied to a cured or dried base coat before the base coat has been cured. The two coatings are then heated to conjointly cure both coating layers. Curing conditions such as described above may be used.

The invention will be further described by reference to the following examples which are presented for the purpose of illustration only and are not intended to limit the scope of the invention.

EXAMPLES

Examples 1 through 7 show the preparation of catalytic tin carboxylate adducts of the present invention at various mole ratios of carboxylic acid functional compound to organotin compound and with various carboxylic acid functional compounds and organotin compounds. Example 8 (comparative) shows the preparation of an epoxy-acid powder coating containing triphenyltin hydroxide as a catalyst. Examples 9 and 10 show the preparation of epoxy-acid powder coating compositions of the present invention containing the catalytic tin carboxylate adduct of Example 1. Example 11 (comparative) shows the preparation of a solventborne epoxy-acid liquid coating composition with a tertiary amine catalyst. Examples 12 and 13 show the preparation of solventborne epoxy-acid liquid coating compositions of the present invention containing the catalytic tin carboxylate adduct of Example 1.

Example 1

A catalytic tin carboxylate adduct of the present invention was prepared by reacting dodecanedioic acid (DDDA) and triphenyltin hydroxide (TPTOH) at a mole ratio of 6.3:1 according to the following procedure.

To a suitable reaction vessel fitted with a nitrogen inlet, a thermocouple, a distillation condenser and receiver flask, and a mechanical stirrer, was added 80.0 grams (0.22 mole) of triphenyltin hydroxide and 320.0 grams (1.4 moles) of dodecanedioic acid. The contents of the reaction vessel were then slowly heated under a blanket of nitrogen to about 120° C. to melt the contents. The temperature was then increased to 135° C. during which time rapid evolution of benzene and a small amount of water occurred. The temperature of the contents was maintained at 135° C. for about three hours. All distillation subsided after about two hours with a total collected distillate of 41 grams. The reaction product melt was poured onto stainless steel sheets to solidify and was then broken into small chunks. The solid catalytic tin carboxylate adduct was ground in a Brinkman Mill to produce a usable catalyst powder. A portion of the catalytic adduct was washed repeatedly with tetrahydrofuran (THF) to remove excess DDDA and was dried for elemental analysis. Results showed the purified solid to be 46.75% carbon, 7.43% hydrogen, and 21.85% tin. Headspace gas chromatographic analysis of the catalytic tin carboxylate adduct indicated less than 10 ppm of benzene at 50° C. The analysis was conducted using Benzene-D6, available from Cambridge Isotope Laboratories, Inc., as an internal standard with a Hewlett Packard HP5890 Gas Chromatography fitted with a HP7694 Headspace Sampler and a HP5970 Mass Selective Detector.

Example 2

A catalytic tin carboxylate adduct of the present invention was prepared by reacting DDDA and TPTOH at a mole ratio of 3.2:1. Using the procedure of Example 1, 40.0 grams (0.11 mole) of TPTOH and 80.0 grams (0.35 mole) of DDDA were reacted to yield a solid catalytic tin carboxylate adduct, with the evolution of 12.7 grams of distillate. Headspace gas chromatographic analysis of the catalytic tin carboxylate adduct indicated 14 ppm of benzene at 50° C.

Example 3

A catalytic tin carboxylate adduct of the present invention was prepared by reacting isostearic acid and TPTOH at a mole ratio of 3:1. Using the procedure of Example 1, 40.0 grams (0.11 mole) of TPTOH and 94.0 grams (0.33 mole) of isostearic acid were reacted to yield a liquid catalytic tin carboxylate adduct, with the evolution of 14.5 grams of distillate Example 4

A catalytic tin carboxylate adduct of the present invention was prepared by reacting DDDA and tritolyltin hydroxide at a mole ratio of 6:1 according to the following procedure.

A suitable reaction flask fitted with nitrogen inlet, thermocouple, dean stark trap, refluxing condenser and mechanical stirrer was flushed with nitrogen. The vessel was charged with 36.7 grams of tritolyltin hydroxide (0.1 mole) and 155.0 grams of dodecanedioic acid (0.6 mole). The reaction was slowly heated to 140° C. with stirring. At 120° C. a distillate started to form and was collected (19.3 grams total). The reaction temperature was maintained for four hours and then vacuum was applied (1.0 mm of Hg) for 30 minutes at 140° C. The vacuum was released and the reaction melt poured into a stainless steel pan to solidify. After cooling to ambient temperature, the resulting solid catalytic tin carboxylate adduct (164.3 grams) was broken into chunks and ground with a mortal and pestle.

Example 5

A catalytic tin carboxylate adduct of the present invention was prepared by reacting lauric and TPTOH at a mole ratio of 2.5:1. Using the procedure of Example 4, 36.7 grams (0.1 mole) of TPTOH and 50.08 grams (0.25 mole) of lauric acid were reacted to yield 62.0 grams of a solid catalytic tin carboxylate adduct, with the evolution of 13.4 grams of distillate.

Example 6

A catalytic tin carboxylate adduct of the present invention was prepared by reacting succinic acid and TPTOH at a mole ratio of 2:1. Using the procedure of Example 4, 73.4 grams (0.6 mole) of TPTOH and 141.71 grams (1.2 moles) of succinic acid were reacted to yield a solid catalytic tin carboxylate adduct, with the evolution of 30.4 grams of distillate.

Example 7

A catalytic tin carboxylate adduct of the present invention was prepared by reacting an acid functional polyester and TPTOH at a mole ratio of 6:1 according to the following procedure.

First, an acid functional polyester was prepared as follows. An initial solvent portion of 177.2 grams n-amyl propionate and 136.2 grams pentaerythritol were charged into a four-neck flask, which served as the reaction vessel, and which was equipped with a thermocouple, a reflux condenser and a stirrer. The initial charge was heated to 125° C. under a nitrogen gas blanket. Charge 2, 659.3 grams methylhexahydrophthalic anhydride, was added dropwise from an addition funnel into the reaction vessel over a period of 1 to 2 hours while maintaining the reaction at 125° C. and under a nitrogen gas blanket. The addition funnel was then rinsed with 10 grams n-amyl propionate. After the completion of the addition, the reaction mixture was cooled to 115° C. and held at that temperature for four hours. Charge 3, 187.2 grams n-propyl alcohol, was then added to the reaction mixture. The reaction was then held at 105° C. under a nitrogen blanket for 30 minutes, after which the reaction mixture was cooled and poured. The reaction mixture had a solids content of 71 percent measured at 110° C. for one hour, an acid value of 183 as measured per American Society of Testing Materials (ASTM) method D-1639, and a weight average molecular weight of 610 as determined by gel permeation chromatography using a polystyrene standard.

A catalytic tin carboxylate adduct was then prepared in a suitable reaction flask fitted with nitrogen inlet, thermocouple, dean stark trap, refluxing condenser and mechanical stirrer that was flushed with nitrogen. The vessel was charged with 22.0 grams of TPTOH (0.06 mole), 100 milliliters of toluene, and 78.12 grams of the acid functional polyester (217 acid equivalent weight) described above. The reaction was slowly heated to reflux (104° C.) with stirring.

The reaction temperature was maintained for 4 hours and then vacuum stripped (1.0 mm of Hg) at 100° C. After cooling to ambient temperature, the resulting solid catalytic tin carboxylate adduct was broken into chunks and ground with a mortal and pestle.

Examples 8 (Comparative), 9, 10

Powder Coating Compositions

Each epoxy-acid powder clear coat composition in Examples 8 through 10 shown below in Table I are shown in amounts of parts by weight, and each composition was processed in the following manner. The components were blended in a Henschel Blender for 30 to 60 seconds. The mixtures were then extruded through a Werner & Pfleider co-rotating twin screw extruder at a 450 RPM screw speed and an extrudate temperature of 113° C. to 115° C. The extruded material was then ground and classified to a particle size of 17 to 27 microns using an ACM1 Grinder (Air Classifying Mill from Micron Powder Systems, Summit, N.J.). The finished powders were electrostatically sprayed onto test panels and evaluated for appearance, mar and humidity resistance. The results are tabulated below in Table II.

Example 8 is a comparative powder coating composition containing TPTOH as a catalyst. Examples 9 and 10 show powder coating compositions of the present invention containing different concentrations of the tin carboxylate adduct of Example 1.

TABLE I

| Ingredient | Example 8 Comparative | Example 9 | Example 10 |
| --- | --- | --- | --- |
| PD 9060[1] | 1205.7 | 1205.7 | 1205.7 |
| DDDA[2] | 294.3 | 294.3 | 194.3 |
| Acrylic Flow Agent[3] | 19.8 | 19.8 | 19.7 |
| Benzoin | 3.3 | 3.3 | 3.3 |
| Microwax C[4] | 9.9 | 9.9 | 9.9 |
| TINUVIN 144[5] | 33.0 | 32.9 | 32.7 |
| TINUVIN 900[6] | 33.0 | 32.9 | 32.7 |
| GCA-1[7] | 33.0 | 33.0 | 33.0 |
| ARMEEN M2C[8] | 4.2 | 0.0 | 0.0 |
| TPTOH[9] | 12.3 | 0.0 | 0.0 |
| Catalytic Adduct of Example 1 | 0.0 | 12.3 | 6.6 |
| Particle size (microns) | 22.9 | 23.4 | 24.5 |
| Gel Time (seconds)[10] | 245 | 144 | 207 |

[1]PD 9060, glycidyl containing polymer having a Tg of 44° C., commercially available from Anderson Development, Inc. made in accordance with U.S. Pat. No. 4,042,645.
[2]Dodecanedioic Acid.
[3]Acrylic flow agent prepared by solution polymerization in xylene of the following monomers: 2% N,N-dimethylaminoethyl methacrylate, 16.8% hydroxyethyl acrylate, and 81.2% 2-ethylhexyl acrylate. The polymerization was at reflux temperature in the presence of t-amyl peracetate (commercially available as LUPERSOL 555M60 from Elf Atochem, Inc.) and t-butyl peracetate. The acrylic flow agent was vacuum stripped (1.0 mm of Hg) at 100° C. to 100% solids.
[4]Wax C Micro Powder, a fatty acid amide (ethylene bis-stearoylamide), commercially available from Hoechst-Celanese.
[5]TINUVIN 144 (2-tert-butyl-2-(4-hydroxy-3,5-di-tert-butylbenzyl)[bis (methyl-2,2,6,6,-tetramethyl-4-piperidinyl)]dipropionate), an ultraviolet light stabilizer available from Ciba-Geigy Corp.
[6]TINUVIN 900 (2-(3',5'-bis(1-methyl-1-phenylethyl)-2'-hydroxyphenyl) benzotriazole), an ultraviolet light stabilizer available from Ciba-Geigy Corp.
[7]GCA-1, an anti-yellowing agent commercially available from Sanko Chemical Corp.
[8]Methyl dicocoamine available from Akzo-Nobel Corp.
[9]Triphenyltin hydroxide commercially available from Elf Atochem North America.
[10]Gel time was measured on a hot plate at 285° F. (140° C.).

The powder coating compositions of Examples 8 to 10 were prepared for testing in the following manner. Test panels, coated with electrocoat primer commercially available from PPG Industries, Inc. as ED-5051, were basecoated, by spray application to a film thickness of about 0.6 mils (15.2 microns), with a black waterborne base coat, commercially available from PPG Industries, Inc. as HWBP-8555. The basecoated panels were then flash baked for 10 minutes at 176° F. (80° C.) before electrostatically spray applying each powder clear coat composition of Examples 8 to 10. The powder coated panels were then cured for 30 minutes at 285° F. (140° C.). The dry film thickness (DFT) of the powder clear was 2.6 to 2.8 mils (66 to 71 microns). The test panels were then tested for appearance using 20° gloss, haze, and DOI as criteria. Also tested were mar resistance and humidity resistance. The results are tabulated in Table H. The mar resistance was tested using the following procedure.

1. Dry Bon-Ami Cleanser (Feldspar/Calcite cleanser manufactured by Faultless Starch/Bon Ami Company, Kansas City, Mo.) was applied to one half of the test panel.
2. The excess cleanser was tapped off so that a thin film of cleanser remained on the test panel.
3. The acrylic finger of an Atlas AATCC Crockmeter, model CM-5 manufactured by Atlas Electric Devices Company, Chicago, Ill., was covered with a two inch by two inch piece of felt cloth, obtainable from Atlas Electric Devices.
4. The cleanser coated panel was rubbed with the felt cloth ten times (ten double rubs) using the Crockmeter.
5. The test was repeated at least once changing the felt cloth after each test.
6. After testing, the panel was washed with water to remove the cleanser and then carefully dried.
7. The 20° gloss was measured using a gloss meter manufactured by Pacific Scientific, on both the unmarred part of the panel and the marred parts of the panel. The difference in gloss was a measure of the mar resistance. The smaller the difference the greater the mar resistance. A percentage of gloss retention was calculated by the following formula: Percent Gloss Retention=[(Difference in Gloss)/(Initial Gloss)]×100. The larger the percent gloss retention, the greater the mar resistance.

TABLE II

| Test | Example 8 Comparative | Example 9 | Example 10 |
| --- | --- | --- | --- |
| 20° Gloss* | 87 | 83 | 80 |
| Haze* | 6 | 10 | 8 |
| DOI* | 97 | 73 | 96 |
| Mar (% Gloss Retention)[1] | 47.9% | 36.8% | 43.0% |
| Acid Etch[2] | 4 | 4 | 5 |
| Humidity (10 Day)[3] | | | |
| 20° Gloss* | 86 | 86 | 86 |
| DOI* | 80 | 88 | 85 |
| Haze* | 7 | 10 | 8 |
| ΔL (Blush)[4] | 0.77 | −0.05 | −0.02 |
| Headspace (for benzene)[5] | | | |
| at 50° C. | 350 ppm | — | <10 ppm |
| at 140° C. | 2000 ppm | — | 15 ppm |

TABLE II-continued

| Test | Example 8 Comparative | Example 9 | Example 10 |
| --- | --- | --- | --- |

*Appearance Properties: 20° Gloss and Haze were measured by a BYK Gardner Haze — Gloss Meter. Higher numbers for gloss indicate better performance and lower numbers for Haze indicate better performance. Haze numbers over 30 are considered unacceptable. Distinction of Image (DOI) was measured by a Hunter Lab's Dorigon II where higher numbers indicate better performance.
[1] Mar was measured by the method described above.
[2] Acid Etch was measured by placing drops of an acid solution composed of 350 grams deionized water, 12 grams $H_2SO_3$ and 0.4 grams $CaSO_4$ onto the surface of the test panels then baking the panels for 30 minutes at 100° F. (38° C.), reapplying the acid solution and baking the test panels for an additional 30 minutes. After cooling, washing with cold water, and blotting the test panels dry, the panels were rated on a scale of 1 to 10 (good to bad) on the basis of quantity and depth of acid marks.
[3] Panels were exposed to 100% humidity at 100° F. for 10 days per ASTM method D-2247.
[4] Blush was measured by taking color readings with a MacBeth Color Eye before and after humidity testing, and examining the $\Delta L$ using the color reading before humidity testing as the control. $\Delta L$ is a measure of lightness/darkness of a color and a $\Delta L$ greater than ±0.5 is visually detectable.
[5] Headspace gas chromatographic analysis for benzene, as described above, of the powder coating composition. Headspace analysis for benzene was not performed on Example 9.

Examples 8 through 10 show that the catalytic tin carboxylate adduct is more catalytic than an organotin compound alone, such as, TPTOH used in comparative Example 8, and thus can be used in smaller quantities to obtain similar results. This is shown by the gel times listed in Table I. The powder coating composition of Example 9 contains an amount of catalytic adduct equivalent to the amount of TPTOH in the comparative powder coating composition of Example 8, and the gel time of the composition of Example 9 is 101 seconds less than the gel time of Example 8.

Example 10 contains an amount of catalytic adduct that is one half the amount of TPTOH in Example 8, and the gel time of the composition of Example 10 is 37 seconds less than the gel time of Example 8.

A major benefit of the use of the catalytic adduct of this invention can be seen by comparing the headspace analysis of benzene of the comparative coating composition of Example 8 with the coating composition of Example 10. Comparative Example 8 evolves 2000 ppm of benzene during the curing bake, 140° C., while the coating composition of Example 10 only evolves 15 ppm during the 140° C. curing bake (see Table II).

Examples 11 (Comparative), 12, 13

Solventborne Coating Compositions

Premix A

Premix A, an uncatalyzed solventborne epoxy-acid clearcoat basemix was prepared by mixing in a suitable container under agitation the following ingredients in the order shown.

| Ingredients | Weight (grams) |
| --- | --- |
| n-Amyl Propionate | 136.8 |
| DOWANOL DPM[1] | 61.2 |
| TINUVIN 328[2] | 45.0 |
| GMA Acrylic Copolymer[3] | 676.8 |
| GMA Acrylic Copolymer[4] | 664.7 |
| n-Propanol | 66.6 |

-continued

| Ingredients | Weight (grams) |
| --- | --- |
| CYMEL 202[5] | 108.0 |
| Acid Functional Polyester[6] | 109.8 |
| Isostearic Acid | 68.4 |
| Octene/Maleic Anhydride Copolymer[7] | 30.6 |
| MODAFLOW[8] | 3.1 |
| Polybutyl acrylate[9] | 14.6 |
| DISLON OX-60[10] | 2.5 |
| TINUVIN 123[11] | 6.7 |
| Acid functional polyester[12] | 853.2 |
| n-Amyl Propionate | 111.6 |

[1] Dipropylene glycol monomethyl ether, available from Dow Chemical Co.
[2] 2-(2'-Hydroxy-3',5'-ditert-amylphenyl) benzotriazole UV light stabilizer available from Ciba-Geigy Corp.
[3] Epoxy functional acrylic copolymer at 65% weight solids prepared by solution polymerization in an 80:20 blend of Solvesso 100 (Mixture of high boiling hydrocarbon solvents available from Exxon Chemical Corp.) :Dowanol PM Acetate (propylene glycol monomethyl ether acetate available from Dow Chemical Co.) of the following monomers (percentages based on total weight of monomers): 60% glycidyl methacrylate, 1% methyl methacrylate, 28.7% butyl methacrylate, 7% styrene, 2% methyl styrene dimer, and 1.3% of a monomer made from hydroxyethyl methacrylate, isophorone diisocyanate, and butanol according to U.S. Pat. No. 5,384,367, Example B. The polymerization was at reflux temperature in the presence of LUPERSOL 555M60 and di-t-amyl peroxide.
[4] Epoxy functional acrylic copolymer at 65% weight solids prepared by solution polymerization in an 80:20 blend of Solvesso 100:Dowanol PM Acetate of the following monomers (percentages based on total weight of monomers): 40% glycidyl methacrylate, 1% methyl methacrylate, 47% butyl methacrylate, and 12% styrene. The polymerization was at reflux temperature in the presence of LUPERSOL 555M60 and di-t-amyl peroxide.
[5] Partially methylated and butylated melamine formaldehyde resin available from CYTEC Industries, Inc.
[6] Acid functional polyester at 80% weight solids prepared from the reaction of 42.9% methylhexahydrophthalic anhydride, 18.2% hexahydrophthalic anhydride, and 38.9% 1-(3-hydroxy-2,2-dimethylpropyl) 3-hydroxy-2,2-dimethylpropionate (ESTER DIOL 204 available from Union Carbide Chemicals and Plastics Company) in a 95:5 blend of butyl acetate:propanol. The reaction was run at 115° C.
[7] Prepared according to U. S. Pat. No. 4,927,868, see Example F.
[8] Acrylic flow agent available from Monsanto.
[9] Flow control agent having a Mw of about 6700 and a Mn of about 2600, made in xylene at 62.5% solids.
[10] Antifoam agent available from King Industries, Inc.
[11] Sterically hindered tertiary amine light stabilizer available from Ciba Geigy Corporation.
[12] Prepared as described above in Example 7.

Premix B

Premix B, a silica grind paste containing the catalytic tin carboxylate adduct of Example 1, was prepared by mixing together the following materials under suitable agitation in a suitable container, then grinding the silica mixture in a horizontal mill to 7 on a Hegman Gauge.

| Ingredients | Weight (grams) |
| --- | --- |
| Acid functional polyester[1] | 155.0 |
| n-Propanol | 355.0 |
| AEROSIL R812[2] | 80.0 |
| Catalyst from Example 1 | 100.0 |

[1] Acid functional polyester at 80% weight solids prepared from the reaction of 21% trimethylolpropane, 23.7% hexahydrophthalic anhydride, and 55.3% methyl hexahydrophthalic anhydride in a 95:5 blend of butyl acetate:propanol. The reaction was run at 115° C.
[2] Highly dispersed hydrophobic amorphous fumed silicon dioxide available from Degussa Corporation.

Premix C

Premix C, a silica grind paste, was prepared by mixing together the following materials under suitable agitation in a suitable container, then grinding the silica mixture in a horizontal mill to a 7 on a Hegman Gauge.

| Ingredients | Weight (grams) |
|---|---|
| Acid functional polyester[1] | 155.0 |
| n-Propanol | 355.0 |
| AEROSIL R812 | 80.0 |

[1]Acid functional polyester described in Premix B above.

Each solventborne epoxy-acid coating composition of Examples 11 to 13 was prepared by mixing together, in a suitable container and under agitation, the following ingredients in the order shown. The amounts are shown as weight in grams.

| Ingredients | Example 11 Comparative | Example 12 | Example 13 |
|---|---|---|---|
| Premix A | 493.2 | 493.2 | 493.2 |
| Premix C | 35.4 | 17.7 | 26.7 |
| ARMEEN DM12D[1] | 3.0 | 0.0 | 0.0 |
| Premix B | 0.0 | 20.7 | 11.7 |

[1]Tertiary amine catalyst commercially available from Akzo-Nobel Corp.

The solventborne epoxy-acid clearcoat compositions of Examples 11 through 13 were tested as follows. Test panels, coated with electrocoat primer commercially available from PPG Industries, Inc. as ED-5000, were first basecoated, by spray application to a film thickness of 0.6 mils (15 microns), with a black waterborne base coat or a silver waterborne basecoat, commercially available from PPG Industries, Inc. as HWB-9517 and HWB-3638, respectively. The base coats were spray applied to the test panels with the spray booth at 60 percent relative humidity. The basecoated panels were then flash baked for 10 minutes at 180° F. (82° C.) before spray applying each clear coat to the flashed base coated test panels. Each clear coat was spray applied in two coats to a film thickness of 1.6 to 1.8 mils (41 to 46 microns) with a 90-second ambient flash between coats and a five minute ambient flash before baking the composite base coat/clear coat film at 285° F. (141° C.) for 30 minutes. The test panels were then tested for appearance using 20° gloss and DOI as criteria Mar resistance was also tested. The results are listed below in Table III.

TABLE III

| | Example 11 Comparative | Example 12 | Example 13 |
|---|---|---|---|
| 20° Gloss | | | |
| Black Basecoat | 81 | 83 | 83 |
| Silver Basecoat | 82 | 83 | 83 |
| DOI | | | |
| Black Basecoat | 92 | 96 | 94 |
| Silver Basecoat | 86 | 79 | 77 |
| Mar | | | |
| % Gloss Retention | 84.4% | 73.8% | 77.6% |
| Viscosity (seconds)[1] | 25.5 | 25.4 | 24.4 |
| Viscosity (at 5 days)[2] | 46.6 | 29.6 | 29.2 |

[1]Initial viscosity, in seconds, was measured with a #4 Ford Cup at 77° F. (25° C.).

TABLE III-continued

| | Example 11 Comparative | Example 12 | Example 13 |
|---|---|---|---|

[2]Viscosity, in seconds, measured after a sealed container containing the coating was exposed to 100° F. (38° C.) for 5 days. Viscosity was measured with a #4 Ford Cup at 77° F. (25° C.). A difference of 10 seconds or greater between the initial viscosity and the 5 day viscosity is considered unacceptable and tends to indicates poor stability.

Examples 11 through 13 show the increased stability of solventborne coating compositions of the present invention which incorporate the catalytic tin carboxylate adduct of this invention. The stability of a coating composition is indicated by the difference between its initial viscosity and its viscosity after five days of aging at 100° F. Table III shows that the comparative coating composition of Example 11 has a viscosity increase of 21.1 seconds after heat aging. The coating composition of Example 12 had an increase in viscosity of 4.2 seconds, and the coating composition of Example 13 had an increase of 4.8 seconds. Increases greater than 10 seconds tend to indicate poor stability of the coating composition.

What is claimed is:

1. A coating composition comprising a polyepoxide, a polyacid curing agent, and a catalytic tin carboxylate adduct comprised of the reaction product of:
   (A) a carboxylic acid functional compound having at least one carboxylic group, the compound selected from the group consisting of
      dicarboxylic acids,
      monocarboxylic acids selected from isostearic acid, lauric acid, tridecanoic acid, myristic acid, and palmitic acid, and
      an acid functional polymer having at least one carboxylic group per molecule; and
   (B) an organotin compound having the general formula:

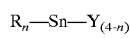
   $$R_n\text{—Sn—}Y_{(4-n)}$$

where
      R is an aryl group chosen from the group consisting of phenyl, substituted phenyl, tolyl, and naphthyl,
      Y is a hydroxyl or halogen group, and
      n is an integer from 1 to 3.

2. The coating composition of claim 1 wherein the carboxylic acid functional compound (A) has the general formula:

   $$R'(COOH)_m$$

where
      R' is a mono, di or polyvalent all or aryl radical, and m is an integer from 1 to 4.

3. The coating composition of claim 1 wherein the dicarboxylic acid is selected from the group consisting of adipic acid, succinic acid, pimelic acid, suberic acid, azelaic acid, sebacic acid, dodecanedioic acid, terephtalic acid, isophthalic acid, phthalic acid, tetrahydrophthalic acid and hexahydrophthalic acid.

4. The coating composition of claim 1 wherein the organotin compound (B) is selected from the group consisting of triphenyltin hydroxide, tritolyltin hydroxide, triphenylchlorotin, triphenylbromotin, tritolylchlorotin, tritolylbromotin, tris-4-ethylphenyl hydroxide, tris-3,5-dimethylphenyl hydroxide, tris-4-methoxyphenyl hydroxide and phenyltin trichloride.

5. The coating composition of claim 1 wherein the mole ratio of carboxylic acid to organotin compound in the catalytic tin carboxylate adduct ranges from about 2:1 to 10:1.

6. The coating composition of claim 1 wherein the mole ratio of carboxylic acid to organotin compound in the catalytic tin carboxylate adduct ranges from about 3:1 to 7:1.

7. The coating composition of claim 1 wherein the catalytic tin carboxylate adduct is present from about 0.05 to 4.0 weight percent based on total solids of the coating composition.

8. The coating composition of claim 1 wherein the catalytic tin carboxylate adduct is present from about 1.2 to 2.0 weight percent based on total solids of the coating composition.

9. The coating composition of claim 1 wherein the catalytic tin carboxylate adduct is a mixture of a mono-aryltin tris-carboxylate and a di-aryltin di-carboxylate where the ratio of tris-carboxylate to di-carboxylate is about 99:1 to 1:99.

10. The coating composition of claim 9 wherein where the ratio of tris-carboxylate to di-carboxylate is about 60:40 to 40:60.

11. The coating composition of claim 9 wherein where the ratio of tris-carboxylate to di-carboxylate is about 90:10 to 50:50.

12. The coating composition of claim 1 wherein the coating composition is a liquid coating composition.

13. The coating composition of claim 1 wherein the coating composition is a powder coating composition.

* * * * *

UNITED STATES PATENT AND TRADEMARK OFFICE
CERTIFICATE OF CORRECTION

PATENT NO.   : 6,251,999 B1
DATED        : June 26, 2001
INVENTOR(S)  : Rardon et al.

It is certified that error appears in the above-identified patent and that said Letters Patent is hereby corrected as shown below:

<u>Column 18,</u>
Line 53, "all" should be -- alkyl --

Signed and Sealed this

Third Day of September, 2002

Attest:

Attesting Officer

JAMES E. ROGAN
Director of the United States Patent and Trademark Office